United States Patent [19]

Kemp

[11] Patent Number: 5,460,962
[45] Date of Patent: Oct. 24, 1995

[54] PERACETIC ACID STERILIZATION OF COLLAGEN OR COLLAGENOUS TISSUE

[75] Inventor: Paul D. Kemp, Winchester, Mass.

[73] Assignee: Organogenesis Inc., Canton, Mass.

[21] Appl. No.: 177,618

[22] Filed: Jan. 4, 1994

[51] Int. Cl.$^6$ .................. C12N 7/06; A61L 2/18
[52] U.S. Cl. ............................... 435/238; 422/28
[58] Field of Search .................. 435/238; 514/553; 422/28

[56] References Cited

U.S. PATENT DOCUMENTS

| | | | |
|---|---|---|---|
| 4,900,721 | 2/1990 | Bansemir et al. | 514/25 |
| 5,116,575 | 3/1992 | Baderstcher et al. | 422/28 |
| 5,298,222 | 3/1994 | O'Leary | 422/28 |

OTHER PUBLICATIONS

Schweizer H. et al, Nature 240 (97):61–2 (1972).
Wenzel K. P. et al, Khirurgiya 29(4): 303–7 (1976).
Starke R. et al, Z Exp Chir Transplan Kunstliche Organe 17(5): 254–8 (1984).
Block, Disinfection, Sterilization and Preservation, 1991, p. 807.
David & Geck, A Guide to Surgical Needles and Suture Characteristics, 1991, pp. 1–5.
Wutzler, P. et al., "Suitability of Peracetic Acid for Sterilization of Media for Mycoplasma Cultures," Journal of Clinical Microbiology, Mar. 1975, pp. 246–249, vol. 1.
Von Versen, R. et al., "The Peracetic acid/low Pressure Cold Sterilization–A new method to Sterilize Corticocancellous Bone and Soft Tissue," Z. exp. Chir. Transplant. kunstl. Organe 22 (1989) pp. 18–21.
Block, Seymour, "Peracetic Acid," Disinfection, Sterilization and Preservation, 4th edition, pp. 172–179, 1993.
Malchesky, P. S., "Peracetic Acid and Its Application to Medical Instrument Sterilization," Artif. Organs. vol. 17, No. 3, pp. 147–152, 1992.
Sabelman, E. E., "Biocompatibility of Tissue Analogs," Biology Biotechnology and Biocompatibility of Collage, Chapter 3, vol. 1, pp. 27–66.

Primary Examiner—Marian C. Knode
Assistant Examiner—S. Saucier
Attorney, Agent, or Firm—Hale and Dorr

[57] ABSTRACT

This invention is directed to the sterilization of collagen and collagenous tissue which is to be used for implantation, repair, or use in a mammalian host in the emerging field of tissue engineering. The sterilants are low concentration peracetic acid solutions in either neutral or high ionic strength that prevent or minimizes the swelling of collagen or collagenous tissue so that the sterilized tissue retains its structural integrity and bioremodelable properties.

4 Claims, No Drawings

PERACETIC ACID STERILIZATION OF COLLAGEN OR COLLAGENOUS TISSUE

FIELD OF THE INVENTION

This invention is in the field of tissue engineering. The invention is directed to the sterilization of collagen and collagenous tissue which is to be used for implantation, repair, or use in a mammalian host. The sterilants are low or dilute concentrations of peracetic acid in either neutral or high ionic strength solutions that permit sterilization of the collagenous tissue with a minimal amount of swelling and dissolution so that the collagen retains its structural integrity and bioremodelable properties.

BACKGROUND OF THE INVENTION

Tissue engineering is an emerging field combining both methods of the engineering and the principles of life sciences to understand the structural and functional relationships in normal and pathological mammalian tissues. The goal of tissue engineering is the development and ultimate application of biological substitutes to restore, maintain or improve tissue functions. Skalak, R. and Fox, C. F., "Tissue Engineering," Alan R. Liss Inc. N.Y. (1988).

One major component of these biological substitutes can be collagen or collagenous tissue. While major strides have been made in this field, and are continuing to be made, there is a constant need for improvement of both the biological substitutes and the processes for making and using them. There currently exists a need for a sterilization method that maintains the biological and physical properties of collagen and collagenous tissues used in tissue engineering. The search for sterilants to sterilize collagen and collagenous tissue has resulted in the use of a variety of different methods.

Physical sterilization methods have included heat, such as boiling, autoclaving, and microwaves. Heat, however, coagulates soft tissues. Additionally, heat at temperatures above 60° to 65° C. will denature collagen. Currently, gamma-irradiation is the preferred technique used to sterilize tissue, using between 0.5 and 2.5 megarads. A recent study has found, however, that collagen is damaged by gamma-irradiation at 1 megarad. Cheung et al., "The Effect of Gamma-Irradiation on Collagen Molecules Isolated Alpha Chains and Crosslinked Native Fibers," *J. Biomedical Material Research*, 24:581–590 (1990). These lower dose ranges are used since irradiation doses in excess of 2 megarads has a detrimental biological effect. Schnell et al., "The Influence of Ionizing Radiation on Various Collagen-Containing Medical Products," *Radiosterilization of Medical Products*, Paper SM92, International Atomic Energy Agency, Vienna (1967).

Known chemical sterilization methods produce chemical reactions that not only sterilize collagen, but also cross-link it. Collagen, cross-linked by chemical sterilization, results in a collagen tissue that is stiffer than uncross-linked collagen, remodels less well, and can evoke an immunological reaction. Thus, the chemical sterilants formaldehyde and glutaraldehyde cross-link collagen and reduce its capacity to remodel after implantation. Kato et al., *Journal Biol. Jt. Surgery*, 73:561 (1991).

Additionally, not all chemical sterilants are suitable for collagen sterilization. Ethyl and isopropyl alcohol are not sporicidal. Organic mercurials are toxic and have an injurious effect on bone osteoinductive protein. Beta-propiolactone is only effective for surface sterilization and, because of its carcinogenicity, it has been removed from the market. Ethylene oxide has been used successfully for sterilization of bone, but can dissolve soft tissue.

All of the sterilization techniques mentioned above have some drawbacks or are only partially effective for the sterilization of collagen. The ideal sterilant must be able to sterilize without altering the essential physical and biological nature of the collagen.

Peracetic acid is a known germicidal sterilant. In medical applications, aqueous or aqueous-ethanol peracetic acid solutions have been used typically to sterilize surfaces of instruments. Malchesky, P. S., "Peracetic Acid and Its Application to Medical Instrument Sterilization," *Artificial Organs*, 17:147–152 (1993). Sterilization of collagenous tissues by peracetic acid using these known techniques, however, is adversely affected by the swelling and dissolution of the collagen caused by the acidity of the solution.

Thus, there continues to be a need for a sterilant that can effectively sterilize collagen intended for use as a biological substitute in tissue engineering applications that maintains the biological and physical properties of the collagen or collagenous material.

SUMMARY OF THE INVENTION

The inventors have discovered that the use of low or dilute concentrations of peracetic acid in either neutral or high ionic strength solutions can prevent or minimize the swelling and dissolution of collagen and collagenous tissue so that the tissue retains its structural integrity and bioremodelable properties. These peracetic acid solutions can be successfully used to sterilize biomedical products containing collagen or collagenous tissue that are to be used for implantation, repair, or use in tissue engineering without the attendant problems due to traditional sterilization methods.

DETAILED DESCRIPTION OF THE INVENTION

The inventors have found that peracetic acid diluted in a neutral or high ionic strength solution is an effective sterilant for collagen and collagenous tissue, preventing or minimizing the swelling and dissolution of the tissue. Peracetic acid is a strong oxidizing agent, sold commercially in approximately 35% concentration. A low concentration or dilute peracetic acid solution will typically contain less than 5% peracetic acid, preferably less than 1%, typically in a range between 0.1% to 0.5%, and more preferred less than 0.5%, typically in a range between 0.02% to 0.1%. The strength of the peracetic acid in the dilute peracetic acid solution is not critical, but it is preferred to use a lower concentration of peracetic acid so that tissue is not damaged. The degree of the microbiological load, or bioburden, of the collagen or collagenous tissue may indicate that a higher concentration of peracetic acid is needed, and the solution can be adjusted accordingly.

The aqueous solution used to dilute the peracetic acid can be any solution that is compatible with collagen, for example, buffered or unbuffered water or saline, or solutions of sodium chloride. The preferred solution is either a buffered solution for ease in adjusting the pH of the dilute peracetic acid solution to neutral pH or a solution of 1M sodium chloride. Storage solutions for the collagenous bone grafts can also be used to dilute the peracetic acid; these are typically phosphate buffered saline solutions.

In one embodiment of this invention, the pH of the low concentration, or dilute, peracetic acid solution is adjusted to neutralize the pH of the solution. Typically, the pH of the dilute peracetic acid solution is first measured with a pH meter or with pH paper. Next, the solution is slowly neutralized by adding a base to the solution. Adjusting the pH is accomplished more easily by first dissolving the base in an aqueous solution. The pH is then adjusted until the pH of the solution is neutral. As used herein, the term "neutral pH", is meant to cover a pH range from about 6.0 to about 8.0 pH. The preferred pH range is from about 7.0 to about 7.5 pH.

In another embodiment, the sterilizing solution is made from peracetic acid diluted in an aqueous solution with a high ionic strength, typically a high salt concentration. As used herein a "high salt concentration" can be any concentration of salt that is effective to prevent collagen from swelling at low pH. Preferably, the aqueous high salt concentration solution can be any concentration from 500 mM to 3M, preferably from about 1M to about 2M. The salt that can be used in this invention can be sodium chloride, potassium chloride, calcium chloride, and the like. This dilute peracetic acid sterilizing solution with high salt concentration does not need to be pH adjusted.

The actual sterilization step is accomplished by soaking or washing the collagen or collagenous tissue with the dilute peracetic acid sterilization solution for a time and under conditions sufficient to achieve sterilization. The time for the sterilization will depend in part upon the size and type of the collagen or collagenous tissue to be sterilized, the manner of applying the sterilization solution, and the amount of bioburden. The sterilization time will typically be from about 5 minutes to about 30 hours.

The peracetic acid sterilization solution can be rinsed from the collagen or collagenous tissue, typically with the sterile water, saline, buffer, or storage media. Alternatively, the tissue graft can be placed directly into the sterile storage media without rinsing.

Since peracetic acid in dilute quantities degrades quickly, the peracetic acid sterilization solution should be used before it reduces. According to S. Block, *Disinfection, Sterilization, and Preservation*, 4th Edition, Lea & Febiger (1993), page 176, for example, a dilute peracetic acid solution of 1% loses half its strength through hydrolysis in 6 days.

Collagen and collagenous tissue that can be sterilized according to this invention can include autogenous, allogenous, and xenogenous materials. Among these biomedical materials that can be sterilized are, but are not limited to, veins, tendons, dermis, heart valves, stomach smooth muscle tissue, and small intestine submucosa.

Collagenous tissue, as used herein, also includes collagen matrix structures and constructs. Since collagen is the basic building block that provides the structural framework for dermis, arteries, veins, tubular structures and most other human organs, the ability of the peracetic acid sterilant of this invention to sterilize collagenous biomaterials without damage is important.

Collagen tissue, matrix biomaterial and constructs, used as implants, in repair, or in a mammalian host, are capable of being remodeled into functional tissue by the host. Dense Fibrillar Collagen (DFC), as described in U.S. Pat. No. 5,378,469, is a homogenous natural collagen that can be remodeled into living tissue and organ equivalents by the host. DFC can be produced in many forms, allowing for the development of many different collagen-based products. These biomedical products have broad applications in organ and tissue replacement therapy because they are designed to be similar to their counter parts in the human body and encourage natural healing.

Although the following invention is illustrated by the examples below for purposes of clarity and understanding, it is not intended to be limited to the examples.

EXAMPLE 1

Preparation of Neutral Peracetic Acid Solution

The following example describes the preparation of the sterilant: neutral peracetic acid solution.

Materials:

Phosphate Buffered Saline (PBS) at 4° C.

Peracetic Acid (35% concentration)

10N Sodium Hydroxide (NaOH)

Pasteur pipette and bulb 1 500 mL sterile Nalgene bottle pH Meter

Phosphate buffered saline (PBS) solution was made from 0.144 grams potassium phosphate monobasic; 3.00 grams sodium phosphate dibasic ($7H_2O$); 9.00 grams sodium chloride; and 1 liter purified water.

Procedure:

1. 349 mL PBS was added to a 500 mL sterile Nalgene bottle.
2. 1.4 mL of peracetic acid was added to the PBS.
3. The bottle containing the peracetic acid solution was capped and shaken gently.
4. A stir bar was added to the bottle and the bottle was placed on a stir plate.
5. The pH of the peracetic acid solution was measured with a pH meter and read between pH 4.0–5.0.
6. With a Pasteur pipette, the solution was neutralized by adding 10N NaOH dropwise until the pH was between 7.0 and 7.2. The total volume of NaOH solution added was about 0.4–0.8 mL. As the pH reaction was slow, the NaOH solution was added slowly.
7. The volume of the solution was increased with PBS to the 500 mL indicator to produce a final peracetic acid concentration of 0.1%.

EXAMPLE 2

Preparation of a High Ionic Strength Peracetic Acid Solution

The following example describes the preparation of the sterilant: dilute, high salt concentration, peracetic acid solution.

Materials:

Peracetic Acid (35% concentration)

Sodium Chloride (NaCl)

1 500 mL sterile Nalgene bottle

Procedure 1. 29.22 grams of NaCl was dissolved to a volume of 500 mls with water.
2. 1.4 ml of 35% peracetic acid was added to make a 0.1% solution.

EXAMPLE 3

Intestinal Collagen Material Graft Sterilization

Materials:

Three, one-foot (1') sections of porcine intestinal collagen material

Freshly prepared, sterile peracetic acid solutions as prepared in Example 1 and Example 2
Sterile Phosphate Buffered Saline (PBS)
Procedure 1. The small intestine of a pig was harvested and then, when trimmed into a sheet, mechanically stripped and cleaned so that the tunica submucosa was delaminated and separated. The submucosa was separated from the small intestine by mechanically squeezing the raw material between opposing rollers. The tunica submucosa of the small intestine is harder and stiffer than the surrounding tissue, and the rollers squeeze the softer components from the submucosa.

2. Three, one-foot samples of cleaned porcine intestinal collagen material were immersed in 100 ml of neutral, 0.1% peracetic acid solution, prepared as described in Example 1, for 16, 40, or 62 hours (three samples for each time point.)

4. One-inch samples were taken from each one-foot sample of intestinal collagen material after incubation for the appropriate time in neutral, 0.1% peracetic acid. These samples were aseptically transferred to either sterile tryptic soy broth (TBS) or thioglycollate media (Thio) and incubated for fourteen days at 37° C. or 30° C., respectively. One-inch samples were also taken from untreated intestinal collagen material and similarly incubated for fourteen days in TSB or Thio to serve as controls.

Results

All experimental peracetic acid treated graft samples, whether incubated for 16, 40, or 62 hours, were sterile after fourteen days in either TSB or Thio. Sections from untreated controls were all contaminated with *Klebsiella pneumoniae* and *Eschericia coli* as seen after 14 days in either TSB or Thio.

EXAMPLE 4

Bacterial Challenge

Materials:

Porcine intestinal collagen material

*Bacillus subtilis* spores

Neutral peracetic acid solution as described in Example 1

Liquid Thioglycollate Broth (Thio)

Tryptic Soy Broth (TSB)

Procedure

1. A sample of intestinal collagen material, as described in Example 3, was inoculated with 2 million *B. subtilis* spores per foot length of material.

2. One-foot samples of inoculated material were immersed in 150 ml of neutral 0.1% peracetic acid solution and incubated for 8 hours or 16 hours (6 samples for each time point).

3. The one-inch samples of neutral peracetic acid-treated intestinal collagen material and controls (inoculated with *B. subtilis* but not peracetic acid treated) were aseptically transferred to either TSB or Thio and incubated for 14 days (Incubated at 37° C. or 30° C., respectively).

Results

All peracetic acid treated samples of intestinal collagen material were sterile. Control samples, spiked with *B. subtilis* spores, gave positive growth in TSB after 1 day incubation and in Thio after 3 days incubation.

EXAMPLE 5

Swelling of Intestinal Collagen Material in Peracetic Acid Solutions

Materials

Porcine intestinal collagen material 0.1% peracetic acid solution in water (pH 3.5)

0.1% peracetic acid solution in phosphate buffered saline (pH 6.1)

0.1% peracetic acid in phosphate buffered saline, neutralized to pH 7.2 as described in Example 1.

0.1% peracetic acid solution in 1M sodium chloride as described in Example 2. (pH 3.3)

Procedure:

Sections of intestinal collagen material (approximately 3 inches long) were prepared as described in Example 3 and blotted dry, weighed and placed in 50 mls of one of the above dilute peracetic acid solutions (the experiment was performed in triplicate). After 19 hours incubation at room temperature, the samples were transferred to fresh solution and left for a further 28 hours. Samples were then removed, blotted briefly to remove surface liquid and re-weighed.

| Solution | Results: | | |
|---|---|---|---|
| | Initial weight Average (grams) | Final Weight Average (grams) | Swelling Average (%) |
| 0.1% PA (in water) pH 3.5 | 3.47 ± 0.3 | 5.07 ± 0.5 | 46 |
| 0.1% PA (in PBS) pH 6.1 | 2.97 ± 0.4 | 1.93 ± 0.1 | −35 |
| 0.1% PA (in PBS) pH 7.2 | 3.43 ± 0.2 | 3.03 ± 0.3 | −11.65 |
| 0.1% PA (in 1M NaCl) | 3.03 ± 0.5 | 2.17 ± 0.6 | −29 |

The sample of intestinal collagen material exposed to 0.1% PA in water swelled 46% over its pre-incubation weight. The other samples exposed to peracetic acid either at pH 6.1 or 7.2 or in 1M NaCl actually lost water compared to initial weight.

EXAMPLE 6

Swelling of DFC in Peracetic Acid Solutions

Materials:

Dense Fibrillar Collagen (DFC) Sheet produced as described in U.S. Pat. No. 5,378 469

0.1% peracetic acid solution in water (pH 3.5)

0.1% peracetic acid solution in phosphate buffered saline (pH 6.1)

0.1% peracetic acid in phosphate buffered saline, neutralized to pH 7.2 as described in Example 1

0.1% peracetic acid solution in 1M sodium chloride as described in Example 2 (pH 3.3)

Method:

Sections of dry DFC sheet (stored dry for more than 6 months) were weighed and placed in 50 mls of one of the above solutions (the experiment was performed in duplicate). After 19 hours incubation at room temperature, the samples were removed, blotted briefly to remove surface liquid and re-weighed.

| Solution | Results: Initial (dry) Weight Average (grams) | Final Weight Average (grams) | Swelling Average (%) |
|---|---|---|---|
| 0.1% PA (in water) pH 3.5 | 0.12 ± 0.03 | 2.05 ± 0.35 | 1682 |
| 0.1% PA (in PBS) pH 6.1 | 0.2 ± 0.02 | 1.32 ± 0.1 | 574 |
| 0.1% PA (in PBS) pH 7.2 | 0.2 ± 0.02 | 1.18 ± 0.12 | 502 |
| 0.1% PA in (in 1M NaCl) | 0.14 ± 0 | 0.47 ± 0.03 | 214 |
| PBS Control (No PA) | 0.15 ± 0.01 | 1.2 ± 0.1 | 700 |

The DFC sample in 0.1% peracetic acid in water swelled more than the other samples. This sample did not dissolve due to covalent crosslink formation which occurs during storage of dry collagen materials. The samples exposed to peracetic acid either at pH 6.1 or 7.2 or in 1M NaCl swelled much less than the sample in 0.1% peracetic acid in water.

EXAMPLE 7

Shrinkage Temperature of DFC Threads Exposed to, Various Peracetic Acid Solutions Methods:

Thread Production

Dense Fibrillar Collagen (DFC) thread production is described in U.S. Pat. No. 5,378,469, incorporated herein by reference. As used for this experiment, a 140 ml syringe containing a 5.0 mg/ml collagen solution in 8.8 mM acetic acid was loaded in a syringe pump (Harvard Apparatus, South Natick, MA) set to infuse at 2.50 ml/min. Silicone tubing (⅛-inch ID) connected the syringe to an 18-gauge blunt stainless steel needle immersed in one end of an 18-foot long, 2-inch diameter PVC trough containing 5L of 20% polyethylene glycol (PEG), MW 8000 (Spectrum Chemicals, New Brunswick, N.J.), in 94 mM sodium phosphate dibasic and 24 mM sodium phosphate monobasic at pH 7.55. A peristaltic pump was used to recirculate the PEG solution such that the fluid velocity at the needle tip was about 4 cm/sec. The circulating PEG solution drew the collagen away from the needle orifice, thus forming a continuous filament. The collagen gelled on contact with the neutral pH solution, and the nascent thread began to dehydrate due to the osmotic pressure gradient formed between the collagen and the PEG solution. The coagulation trough was configured such that the residence time of the thread in the bath was approximately 4 minutes. As the thread accumulated, it was manually transferred to a 6 foot long trough filled with 5.5 mM sodium phosphate dibasic, 0.5 mM potassium phosphate monobasic and 75 mM NaCl at pH 7.10, and remained there for 5 to 10 minutes.

The thread was then partially dehydrated by passing it through a 2 foot long trough containing 70% isopropanol, and dried under tension by drawing it over a series of Teflon pulleys inside a cabinet heated with air blowers. To prevent the collagen from being heat denatured, the thread was kept in motion, and was always at least 15 cm from the blowers. Finally, the thread was spooled onto a level winding device.

The tension on the thread during the drying was such that its length doubled before it emerged dry from the cabinet. The total residence time in the cabinet was approximately 3 minutes.

Once the filament was threaded through the entire system, it could be produced continuously; the operator needed only to keep the coagulation and rinsing reservoirs filled with enough slack to permit reeling.

Shrinkage Temperature Measurement

Shrinkage temperature, a measure of the stability of the collagen triple helix, was measured by immersing a 5 to 7 cm loop of thread loaded with 2.5 g in 1.0 mM potassium phosphate monobasic, 11 mM sodium phosphate dibasic, and 150 mM NaCl at pH 7.30, and heating at 1° C. per minute until shrinkage occurred. The temperature at which the sample shrank by at least 10% was recorded as the shrinkage temperature.

Peracetic Acid Treatment

Lengths of collagen thread were exposed to the following solutions for 20 minutes:

1) 0.1% peracetic acid solution in water (pH 3.5);

2) 0.1% peracetic acid solution in phosphate buffered saline (pH 6.1)

3) 0.1% peracetic acid in phosphate buffered saline, neutralized to pH 7.2 as described in Example 1;

4) 0.1% peracetic acid solution in 1M sodium chloride as described in Example 2 (pH 3.3).

| Solution | Results: Initial Shrinkage Temperature (°C.) | Final Shrinkage Temperature (°C.) |
|---|---|---|
| 0.1% PA (in water) pH 3.5 | 47.5 ± 1.0 | Dissolved |
| 0.1% PA (in PBS) pH 6.1 | 47.5 ± 1.0 | 45.5 ± 1.0 |
| 0.1% PA (in PBS) pH 7.2 | 47.5 ± 1.0 | 47.5 ± 0.5 |
| 0.1% PA (in 1M NaCl) | 46.5 ± 0.5 | 47.0 ± 1.0 |

The shrinkage temperature was not affected by treatment with peracetic acid. The collagen threads dissolved in 0.1% peracetic acid in water, but remained intact in the other solutions.

Although the foregoing invention has been described in some detail by way of illustration and example for purposes of clarity of understanding, it will be obvious to one skilled in the art that certain changes and modifications may be practiced within the scope of the appended claims.

I claim:

1. A method for sterilizing collagen or collagenous tissue comprising veins, tendons, dermis, heart valves, stomach smooth muscle tissue and small intestine submucosa comprising contacting said collagen or collagenous tissue with a solution consisting essentially of peracetic acid in the concentration range of 0.02% to 1.0% and a neutralized pH of about 6.0 to about 8.0 in order to sterilize said collagen or collagenous tissue with no or a minimal amount of swelling and dissolution in comparison with use of an unneutralized peracetic acid solution.

2. The method of claim 1 wherein the peracetic acid concentration is about 0.1%.

3. A method for sterilizing collagenous tissue comprising veins, tendons, dermis, heart valves, stomach smooth muscle tissue an small intestine submucosa comprising contacting said collagen or collagenous tissue with a solution consisting essentially of peracetic acid in the concentration range of 0.02% to 1.0% and a salt concentration from about 1M to about 2M in order to sterilize said collagen or collagenous tissue with no or a minimal amount of swelling and dissolution in comparison with use of a peracetic acid solution without salt.

4. The method of claim 3 wherein the peracetic acid concentration is about 0.1%.

* * * * *